United States Patent
Agoston et al.

(10) Patent No.: US 6,995,278 B2
(45) Date of Patent: Feb. 7, 2006

(54) ANTIANGIOGENIC AGENTS

(75) Inventors: Gregory E. Agoston, Germantown, MD (US); Victor Pribluda, Silver Spring, MD (US); Anthony M. Treston, Rockville, MD (US); Shawn J. Green, Vienna, VA (US)

(73) Assignee: Entre Med, Inc., Rockville, MD (US)

( * ) Notice: Subject to any disclaimer, the term of this patent is extended or adjusted under 35 U.S.C. 154(b) by 0 days.

(21) Appl. No.: 09/779,331

(22) Filed: Feb. 8, 2001

(65) Prior Publication Data

US 2002/0147183 A1 Oct. 10, 2002

Related U.S. Application Data (63) Continuation of application No. 09/641,327, filed on Aug. 18, 2000.

(51) Int. Cl.
*A61K 31/56* (2006.01)
*C07J 41/00* (2006.01)
*C07J 1/00* (2006.01)

(52) U.S. Cl. .................. 552/614; 552/518; 552/519; 552/522; 552/625; 552/626; 552/627; 514/182

(58) Field of Classification Search .................. 552/625, 552/626, 627, 505, 614, 518, 519, 522; 514/169, 514/182
See application file for complete search history.

(56) References Cited

U.S. PATENT DOCUMENTS

| | | | |
|---|---|---|---|
| 2,584,271 A | 2/1952 | Huffman | |
| 2,846,453 A | 8/1958 | Hoehn | |
| 3,166,577 A | 1/1965 | Ringold et al. | |
| 3,410,879 A | 11/1968 | Smith et al. | |

(Continued)

FOREIGN PATENT DOCUMENTS

| | | | |
|---|---|---|---|
| CA | 2339368 A1 | * | 2/2000 |
| CA | 2385096 | * | 4/2001 |
| DE | 1907330 | | 10/1969 |
| DE | 2 004 516 | | 9/1970 |
| DE | 3625315 | | 1/1998 |
| GB | 587081 | | 12/1960 |
| GB | 857080 | | 12/1960 |
| GB | 1570597 | * | 7/1980 |
| JP | 39-5480 B | | 4/1964 |
| JP | 41 000100 A | | 1/1966 |
| JP | 42-928 B | | 1/1967 |
| JP | 63090763 | | 4/1988 |

(Continued)

OTHER PUBLICATIONS

Nambara et al. (DN 82:43650, CAPLUS, abstract of Chem.Pharm. Bull. (1974), 22(10), 2455–7).*
Brueggemeier et al. (J. Med. Chem. (1996), 39, 1917–1923).*

(Continued)

*Primary Examiner*—Sabiha Qazi
(74) *Attorney, Agent, or Firm*—Kilpatrick Stockton LLP

(57) ABSTRACT

Compositions and methods for treating mammalian disease characterized by undesirable angiogenesis by administering derivatives of 2-methoxyestradiol of the general formula:

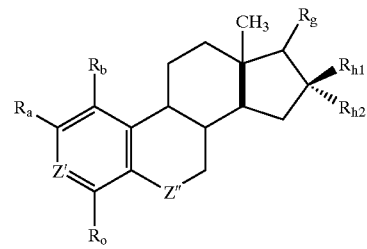

wherein the variables are defined in the specification.

8 Claims, 1 Drawing Sheet

U.S. PATENT DOCUMENTS

| | | | |
|---|---|---|---|
| 3,470,218 A | 9/1969 | Farah | |
| 3,492,321 A | 1/1970 | Crabbe | |
| 3,496,272 A | 2/1970 | Kruger | |
| 3,562,260 A | 2/1971 | De Ruggieri et al. | |
| 3,956,348 A | 5/1976 | Hilscher | |
| 4,172,132 A | 10/1979 | Draper et al. | |
| 4,212,864 A | 7/1980 | Tax | |
| 4,307,086 A | 12/1981 | Tax | |
| 4,444,767 A | 4/1984 | Torelli et al. | |
| 4,522,758 A | 6/1985 | Ward et al. | |
| 4,634,705 A | 1/1987 | DeBernardis et al. | |
| 4,743,597 A | 5/1988 | Javitt et al. | |
| 4,994,443 A | 2/1991 | Folkman et al. | |
| 5,001,116 A | 3/1991 | Folkman et al. | |
| 5,135,919 A | 8/1992 | Folkman et al. | |
| 5,504,074 A * | 4/1996 | D'Amato et al. | 514/182 |
| 5,521,168 A | 5/1996 | Clark | |
| 5,621,124 A | 4/1997 | Seilz et al. | |
| 5,643,900 A | 7/1997 | Fotsis et al. | |
| 5,661,143 A * | 8/1997 | D'Amato et al. | 514/182 |
| 5,892,069 A * | 4/1999 | D'Amato et al. | 552/627 |
| 5,958,892 A | 9/1999 | Mukhopadhyay et al. | |
| 6,011,023 A | 1/2000 | Clark et al. | |
| 6,051,726 A | 4/2000 | Sachdeva et al. | |
| 6,054,598 A * | 4/2000 | Sachdeva et al. | 552/627 |
| 6,136,992 A * | 10/2000 | Ram et al. | 552/614 |
| 6,200,966 B1 | 3/2001 | Stewart | |
| 6,239,123 B1 | 5/2001 | Green et al. | |
| 6,448,419 B1 * | 9/2002 | Paaren et al. | 552/505 |
| 6,730,665 B1 | 5/2004 | Maran et al. | |
| 2002/0035098 A1 | 3/2002 | Slaga et al. | |
| 2003/0027803 A1 | 2/2003 | Slaga et al. | |
| 2003/0036539 A1 | 2/2003 | Slaga et al. | |
| 2003/0073674 A1 | 4/2003 | Slaga et al. | |
| 2004/0053906 A1 | 3/2004 | Slaga et al. | |

FOREIGN PATENT DOCUMENTS

| | | |
|---|---|---|
| JP | 11-209322 | 8/1999 |
| SU | 1240038 A1 | 10/1996 |
| WO | WO 87/02367 A3 | 4/1987 |
| WO | WO 88/08002 A1 | 10/1988 |
| WO | WO 90/15816 A1 | 12/1990 |
| WO | WO 93/03729 | 3/1993 |
| WO | WO 95/04535 | 2/1995 |
| WO | WO 98/32763 A1 | 7/1998 |
| WO | WO 98/40398 | 9/1998 |
| WO | WO 99/01142 A1 | 1/1999 |
| WO | WO 99/33858 A3 | 7/1999 |
| WO | WO 99/33859 A2 | 7/1999 |
| WO | WO 00/07576 A2 | 2/2000 |
| WO | WO 00/10552 A2 | 3/2000 |
| WO | WO 00/66095 A2 | 11/2000 |
| WO | WO 00/68246 A1 | 11/2000 |
| WO | WO 01/27132 A1 | 4/2001 |
| WO | WO 01/85755 A1 | 11/2001 |

OTHER PUBLICATIONS

Pert et al. (DN 111:233338, CAPLUS, abstract of Australian J. of Chem. (1989), 42(3), 421–32).*

Li et al. (DN 103:65176, CAPLUS, abstract of Molecular Pharmacology (1985), 27(5), 559–65).*

Lilopristone/(1–[4–Dimethylamino)phenyl]–17–hydroxy–17–(3–hydroxy–1–propenyl)estra–4, 9–diene–3–one; AK 98734 *Dict. of Drugs (1990), Dict. of Steroids (1991), Dict. of Org. Cmpds (6th Ed) (1996), Dict. of Pharm. Agents (1997)*, Title: Lilopristone/1–4[4–(Dimethylamino)phenyl]–17–hydroxy–17–(3–hydroxy–1–propenyl) estra–4, 9–diene–3–one; AK 98734.

*The Merck Index 11th Edition*, (paragraphs 583–584), pp. 88, 1989.

*Journal of Endocrinology*, Steroidal regulation of oestradiol–17B dehydrogenase activity of the human breast cancer cell line MCF–7, vol./Iss: 188(1), pp.: 149–154, Jul. 1988.

*Cancer Research*, Natural Estrogens Induce Modulation of Microtubules in Chinese Hamster V79 Cells in Culture, vol./Iss: 55, pp. 1863–1868, May 1, 1995.

Attalia et al., 2–Methoxyestradiol Arrests Cells in Mitosis without Depolarizing Tubulin, *Biochemical and Biophysical Research Communications*, vol./Iss: 228, pp. 467–473, 1996.

Ayala et al., The Induction of Accelerated Thymic Programmed Cell Death During Polymicrobial Sepsis: Control by Corticosteroids but not Tumor Necrosis Factor (Abstract only), vol./Iss: 3 (4), pp. 259–267, Apr. 1995.

Banik et al., Orally Active Long–Acting Estrogen (3–(2–propynyloxy)–estra–1,3,5, (10)–triene–17.beta.–ol trimethylacetate), *Steroids*, vol./Iss: 16 (3), pp. 289–296, 1970.

Bardon et al., Steroid Receptor–Mediated Cytotoxicity of an Antiestrogen and and Antiprogestin in Breast Cancer Cells (Abstract only), *Cancer Research*, vol./Iss: 47 (5), pp. 1441–1448, Mar. 1, 1987.

Bhat et al., Estradiol–induced Mitotic Inhibition in the Bursa of Fabricius of Male Domestic Duckling, *Mikroskopie*, vol./Iss: 39, pp. 113–117, May 1982.

Blagosklonny et al., Raf–1/bcl–2 Phosphorylation: A Step from Microtubule Damabe to Cell Death, *Cancer Research*, vol./Iss: 57, pp. 130–135, Jan. 1, 1997.

Blickenstaff et al., Estrogen–Catharanthus (Vinca) Alkaloid Conjugates, *Cytotoxic Estrogens in Hormone Receptive Tumors*, pp. 89–105, 1980.

Boye et al., 185. Deaminocolchinyl Methyl Ether. Synthesis from 2,3,4,4'–Tetramaehoxybiphenyl–2–carbaldehyde. Comparison of Antitubulin Effects of, *Helvetica Chimica Acta*, vol./Iss: 72, pp. 1690–1696, 1989.

Brodie, A.M., Aromatase Inhibitors in the Treatment of Breast Cancer (Abstract only), *Journal of Steroid Biochemistry and Molecular Biology*, vol./Iss: 49 (4–6), pp. 281–287, Jun. 1994.

Brosens et al., Comparative Study of the Estrogenic Effect of Ethinylestradiol and Mestranol on the Endometrium, *Laboratory for Gynecological Physiopatholog*, vol./Iss: 14 (6), pp. 679–685, Dec. 1, 1976.

Castagnetta, L. et al., Simple Approach to Measure Metabolic Pathyways of Steroids in Living Cells, *Journal of Chromatography*, vol./Iss: 572, pp. 25–39, Dec. 6, 1991.

Chasserot–Golaz et al., Biotransformation of 17.beta.–hydroxy–11.beta.–(4–dimethylaminophenyl)17.alpha.1–propynl–estra–4,9–diene–3–one (RU486) in Rat Hepatoma Variants (Identifier only), *Biochemical Pharmacology*, vol./Iss: 46 (11), pp. 2100–2103, Jan. 1, 1993.

Chen et al., A New Synthetic Route to 2– and 4–Methoxyestradiols by Nucleophilic Substitution, *Steroids*, vol./Iss: 47 (1), pp. 63–66, Jan. 1986.
Chen et al., Synthesis of 11.beta.–(4–dimethyiaminophenyl)–17.beta–hydroxy–17. alpha.–(1–propyl) estra–4, 9–dien–3–one (RU486) (Identifier only), *Nanjing Yaoxueyuan Xuebao*, vol./Iss: 17 (4), pp. 282–285, 1986.
Cohen et al., Novel Total Synthesis of (+)–Estrone 3–Methyl Ether, (+)–13B–Ethyl–3–methoxygona–1,3, 5(10–triene–17–one, and (+)–Equilenin 3–Methyl Ether, *The Journal of Organic Chemistry*, vol./Iss: 6, pp. 681–685, Mar. 21, 1975.
Collins et al., The Structure and Function of Estrogens. XI* Synthesis of (+/–)–7(8–11 α) abeo–Estradiol and its 9,11–Didehydro Derivative, *Aust. Journal of Chemistry*, vol./Iss: 45, pp. 71–97, 1992.
Crum, R. et al., A New Class of Steroids Inhibits Angiogenesis in the Presence of Heparin or a Heparin Fragment, *Science*, vol./Iss: 230, pp. 1375–1378, Dec. 20, 1985.
Cummings et al., Apoptosis, *The American Journal of Surgical Pathology*, vol./Iss: 21 (1), pp. 88–101, 1997.
Cushman et al., Synthesis, Antitubulin and Antimitotic Activity, and Cytotoxicity of Analogs of 2–Methoxyestradiol, an Endogenous Mammalian Metabolite of Estradiol that, *Journal of Medical Chemistry*, vol./Iss: 38 (12), pp. 2041–2049, 1995.
Cushman et al., Synthesis of Analogs of 2–Methoxyestradiol with Enhanced inhibitory Effects of Tubulin Polymerization and Cancer Cell Growth, *Journal of Medical Chemistry*, vol./Iss: 40 (15), pp. 2323–2334, 1997.
D'Amato et al., 2–Methoxyestradiol, an Endogenous Mammalian Metabolite, Inhibits Tubulin Polymerization by Interacting at the Colchicine Site, *Proceedings of the National Academy of Science USA*, vol./Iss: 91, pp. 3964–3968, Apr. 1994.
Dvir et al., Thin–layer Chromatography of DANSYL–oestrogens, *Journal of Chromatography*, vol./Iss: 52, pp. 505–506, Nov. 4, 1970.
Epe et al., Microtubular Proteins as Cellular Targets for Carcinogenic Estrogens and Other Carcinogens, *Mechanisms of Chromosome Distribution and Aneuploidy*, pp. 345–351, 1989.
Evans et al., A Convergent Total Synthesis of (+)– Colchicine and (+)– Desacetamiodoisocolchicine, *Journal of the American Chemical Society*, vol./Iss: 103, pp. 5813–5821, Sep. 23, 1981.
Fishman, J., Synthesis of 2–Methoxyestrogens, *Journal of the American Chemical Society*, vol./Iss: 80, pp. 1213–1216, Mar. 5, 1998.
Fitzgerald, Molecular Features of Colchicine Associated with Antimitotic Activity and Inhibition of Tubulin Polymerization, *Biochemical Pharmacology*, vol.Iss: 25, pp. 1383–1387, Jun. 15, 1976.
Fotsis et al., The Endogenous Oestrogen Metabolite 2–Methoxyoestradiol Inhibits Angiogenesis and Suppresses Tumor Growth, *Nature*, vol./Iss: 368, pp. 237–239, Mar. 1, 1994.
Getahun et al., Synthesis of Alkoxy–Substituted Diaryl Compounds and Correction of Ring Separation with Inhibition of Tubulin Polymerization: Differential Enhancement of Inhibitory Effects Under Suboptimal Polymerization, *Journal of Medical Chemistry*, vol./Iss: 35 (6), pp. 1058–1067, Mar. 20, 1992.

Gross et al., Inhibition of Tumor Growth, Vascularization, and Collagenolysis in the Rabbit Cornea by Medroxyprogesterone, *Proceedings of the National Academy of Science USA*, vol./Iss: 78 (2), pp. 1176–1180, Feb. 1981.
Guangrong et al., Effect of Components of Crowth Ether Copper(1)Iodide Mixed Catalyst on Nucleophilic Substitution of Bromoestrogen (Abstract No. 195225), *Chemical Abstracts*, vol./Iss: 111 (21), pp. 818, col. 1, Nov. 20, 1989.
Haldar et al., Bc12 is the Guardian of Microtubule Integrity, *Cancer Research*, vol./Iss: 57, pp. 229–233, Jan. 15, 1997.
Hamel et al., Interactions of 2–Methoxyestradiol, an Endogenous Mammalian Metabolite, with Unpolymerized Tubulin and with Tubulin Polymers, *Biochemistry*, vol./Iss: 35 (4), pp. 1304–1310, 1996.
Hartley–Asp et al., Diethylstilbestrol Induces Metaphase Arrest and Inhibits Microtubule Assembly, *Mutation Research*, vol./Iss: 146 (4), pp. 231–235, Aug. 1985.
He et al., A Versatile Synthesis of 2–Methoxyestradiol, an Endogenous Metabolite of Estradiol which Inhibits Tubulin Polymerization by Binding to the Colchicine Biding Site, *Bioorganic & Medicinal Chemistry Letters*, vol./Iss: 4 (14), pp. 1724–1728, 1994.
Huber et al., Tubulin Binding of Conformationally Restricted Bis–Aryl Compounds, *Bioorganic & Medicinal Chemistry Letters*, vol./Iss: 1 (5), pp. 243–246, 1991.
Josefsson et al., Suppression of Type II Collagen–Induced Arthritis by the Endogenous Estrogen Metabolite 2–Methoxyestradiol, *Arthritis & Rheumatism*, vol./Iss: 40 (1), pp. 154–163, Jan. 1997.
Kabarity et al., Further Investigations on the cytological effects of some contraceptives, *Mutation Research*, vol./Iss: 135, pp. 181–188, 1984.
Kelly et al., The Stimulation of Prostaglandin Production by Two Antiprogesterone Steroids in Human Endometrial Cells (Abstract only), *Journal of Clinical Endocrinology Metabolism*, vol./Iss: 62 (6), pp. 1116–1123, Jun. 1986.
Klauber et al., Inhibition of Angiogenesis and Breast Cancer in Mice by the Microtubule Inhibitors 2–Methoxyestradiol and Taxol, *Cancer Research*, vol./Iss: 57, pp. 1765–1771, 1997.
Lebras, J. et al., Activation and Regioselective Ortho–Functionalization of the A–Ring of B–Estradiol Promoted by "Cp": An Efficient Organometallic Procedure for the Synthesis of 2–Methoxyestradiol, *Organometallics*, vol./Iss: 16, pp. 1765–1771, 1997
Lin et al., Interactions of Tubulin with Potent Natural and Synthetic Analogs of the Antimitotic Agent Combretastain: A Structure–Activity Study, *Molecular Pharmacology*, vol./Iss: 34 (2), pp. 200–208, Aug. 1988.
Lincoln et al., Conformation of Thiocolchicine and Two B–Ring–Modified Analogues Bound to Tubulin Studied with Optical Spectroscopy, *Biochemistry*, vol./Iss: 30 (5), pp. 1179–1187, Feb. 5, 1991.
Lottering et al., Effects of the 17β–Estradiol Metabolities on Cell Cycle Events in MCF–7 Cells, *Cancer Research*, vol./Iss: 52, pp. 5926–5932, Nov. 1, 1992.
Lottering et al., 17βEstradiol Metabolites Affect Some Regulators of the MCF–7 Cell Cycle, *Cancer Letters*, vol./Iss: 110, pp. 181–186, 1996.
Mayol et al., Ethynylestradiol–Induced Cell Proliferation in Rat Liver Involvement of Specific Populations of Hepatocytes (Abstract only), *Carcinogenesis*, vol./Iss: 12 (12), pp. 2381–2388, 1992.

Meikrantz et al., Apoptosis and the Cell Cycle, *Journal of Cellular Biochemistry*, vol./Iss: 58, pp. 160–174, Jun. 1995.

Miller et al., Synthesis and Structure–Activity Profiles of A–Homoestranes, the Estratropones, *Journal of Medicinal Chemistry*, vol./Iss: 40, pp. 3836–3841, 1997

Morgan et al., Calcium and Oestrogen Interactions upon the Rat Thymic Lymphocyte Plasma Membrane, *Biochemical and Biophysical Research Communications*, vol./Iss: 72 (2), pp. 663–672, Sep. 20, 1976.

Mukhopadhyay et al., Induction of Apoptosis in Human Lung Cancer Cells after Wild–Type p53 Activation by Methoxyestradiol, *Oncogene*, vol./Iss: 14, pp. 379–384, 1997.

Mukundan et al., Liver Regeneration in Oral Contraceptive Treated Female Rat—Effects of Moderate Malnutrition, *Hormone and Metabolic Research*, vol./Iss: 16, pp. 641–645, Dec. 1984.

Nakagawa–Yagi et al., The Endogenous Estrogen Metabolite 2–Methoxyestradiol Induces Apoptotic Neuronal Cell Death In Vitro, *Life Sciences*, vol./Iss: 57 (17), pp. 1461–1467, 1996.

Nakamura et al., Studies on the Total Synthesis of di–Colchicine. I. Synthesis 3–Hydroxy–9, 10, 11–trimethoxy–1,2,3,4,6,7–hexahydro–5H–dibenso[a,c] cycloheptatrien–5–one, *Chemical and Pharmaceutical Bulletin*, vol./Iss: 10, pp. 281–290, 1962.

Nambara et al., Studies on Steroid Conjugates. III. New Synthesis of 2–Methoxyestrogens, *Chem. Pharm. Bulletin*, vol./Iss: 18 (3), pp. 474–480, Mar. 1970.

Napolitano et al., 11 Beta–Substituted Estradiol Derivatives. 2. Potential Carbon–11 and Iodine–Labeled Probes for the Estrogen Receptor (Abstract only), *Journal of Medical Chemistry*, vol./Iss: 38 (14), pp. 2774–2779, Jul. 7, 1995.

Nishigaki et al., Anti–Proliferative Effect of 2–Methoxyestradiol on Cultured Smooth Muscle Cells from Rabbit Aorta, *Atherosclerosis*, vol./Iss: 113, pp. 167–170, 1995.

Ochs et al., Effect of Tumor Promoting Contraceptive Steroids on Growth and Drug Metabolizing Enzymes in Rat Liver (Abstract only), *Cancer Research*, vol./Iss: 46 (3), pp. 1224–1232, 1986.

Oppolzer et al., 177. The Enantioselective Synthesis of (+)–Estradiol from 1,3–Dihydrobenzo[c] thiophene–2,2–dioxide by Successive Thermal $SO_2$–Extrusion and Cycloaddition Reactions, *Helvetica Chimica Acta*, vol./Iss: 63, pp. 1703–1707, 1980.

Parthasarathy et al., Antioxidant: A New Role for RU–486 and Related Compounds (Abstract only), *Journal of Clinical Investigation*, vol./Iss: 94 (5), pp. 1990–1995, Nov. 1994.

Paull et al., Identification of Novel Antimitotic Agents Acting at the Tubulin Level by Computer–assisted Evaluation of Differential Cytotoxicity Data, *Cancer Research*, vol./Iss: 52, pp. 3892–3900, Jul. 15, 1992.

Poli et al., Tumor Necrosis Factor α Functions in an Autocrin Manner in the Induction of Human Immunodeficiency Virus Expression, *Proceeding of the National Academy of Science USA*, vol./Iss: 87, pp. 782–785, Jan. 1990.

Ravindra, R., Effect of Estradiol on the in vitro Assembly of Rat Brain Tubulin, *Journal of Indian Institute of Science*, vol./Iss: 64 (3), pp. 27–35, Mar. 1983.

Sakakibara et al., Effects of Diethylstilbestrol and its Methl Ethers on Aneuploidy Induction and Microtubule Distribution in Chinese Hamster V79 cells, *Mutation Research*, vol./Iss: 263, pp. 269–276, Aug. 1991.

Sato et al., Effect of Estradiol and Ethynylestradiol on Microtubule Distribution in Chinese Hamster V79 Cells, *Chemical and Pharmaceutical Bulletin*, vol./Iss: 40 (1), pp. 182–184, Jan. 1992.

Sato et al., Disruptive Effect of Diethylstibestrol on Microtubules, *Gann*, vol./Iss: 75, pp. 1046–1048, Dec. 1984.

Sawada et al., Colchicine–Like Effect of Diethylstilbestrol (DES) on Mammalian Cells in Vitro, *Mutation Research*, vol./Iss: 57, pp. 175–182, May 1978.

Seergers et al., Cyclic–AMP and Cyclic–GMP Production in MCF–7 Cells Exposed to Estradiol–17 Beta, Catecholestrogens and Methoxy–Estrogens in MCF–7 Cells (Meeting Abstract only), *Joint MCI–1st Symposium. Third 1st International Symposium. Biology and Therapy of Breast Cancer*, Sep. 25, 1989.

Seegers, J.C. et al., The Cytotoxic Effects of Estradiol–17B, Catecholestradiols and Methoxyestradiols on Dividing MCF–7 and Hela Cells, *Journal of Steroid Biochemistry*, vol./Iss: 32 (6), pp. 797–809, 1989.

Sharp et al., Diethylstilbestrol: the Binding and Effects of Diethylstilboestrol upon the Polymerisation and Depolymerisation of Purified Microtubule Protein in vitro, *Carcinogens*, vol./Iss: 6 (6), pp. 865–871, Jun. 1985.

Spicer et al., Catecholestrogens Inhibit Proliferation and DNA Synthesis of Porcine Granulosa Cells in Vitro: Comparison with Estradiol, 5α–dihydrotestosterone, Gonadotropins and Catecholamines, *Molecular and Cellular Endocrinology*, vol./Iss: 64, pp. 119–126, 1989.

Sternlicht et al., Colchicine Inhibition of Microtubule Assembly via Copolymer Formation, *The Journal of Biological Chemistry*, vol./Iss: 254 (20), pp. 10540–10550, Oct. 25, 1979.

Sun et al., Antitumor Agents. 139. Synthesis and Biological Evaluation of Thiocolchicine Analogs 5,6–Dihydro–6(S)–(acyloxy)–and 5,6–Dihydro–6(S)–[(acyloxy)methyl]–1,2,3–, *Journal of Medicinal Chemistry*, vol./Iss: 36 pp. 544–551, Mar. 5, 1993.

Sunagawa et al., Synthesis of Colchicine; Synthesis of di–'Demethyoxydeoxy–hexahydrocolchicine, *Chem. Pharm. Bulletin*, vol./Iss: 9, pp. 81–83, 1961.

Teranishi, et al., Methylation of Catechol Estrogen with Diazomethane, *Chemical and Pharamecutical Bulletin*, vol./Iss: 31 (9), pp. 3309–3314, Sep. 1983.

Tishler et al., Microtubule–Active Drugs Taxol, Vinblastine, and Nocodazole Increase the Levels of Transcriptionally Active p53, *Cancer Research*, vol./Iss: 55, pp. 6021–6025, Dec. 15, 1995.

Tsutsui et al., Comparison of Human Versus Syrian Hamster Cells in Culture for Induction of Mitotic Inhibition, Binucleation and Multinucleation, Following Treatment with Four Aneuploidogens, *Toxicology* in Vitro, vol./Iss: 4 (1), pp. 75–84, 1990.

Utne et al., The Synthesis of 2– and 4–Fluoroestradiol, *Journal of Organic Chemistry*, vol./Iss: 33 (6), pp. 2469–2473, Jun. 1968.

Van Geerestein et al., Structure of 11.beta.–(4–(dimethylamino)phenyl)–17.beta.–hydroxy–17.alpha.–(2–propenyl) estra–4,9–dien–3–one (Identifier only), *Acta Crystall Ogr., Sect. C: Cryst. Struct. Commun.*, vol./Iss: C43 (2), pp. 319–322, 1987.

Van Tamelen et al., The Synthesis of Colchicine, *Tetrahedron*, vol./Iss: 14, pp. 8–34, Sep. 1991.

Wang, Z. et al., An Optimized Synthesis of 2–Methoxyestradiol, a Naturally Occurring Human Metabolite with Anticancer Activity, *Synth. Commun.*, vol./Iss: 28 (23), pp. 4431–4437, 1998.

Wheeler et al., Mitotic Inhibitiion and Aneuploidy Induction by Naturally Occurring and Synthetic Estrogens in Chinese Hamster Cells in Vitro, *Mutation Research*, vol./Iss: 171, pp. 31–41, 1986.

Wheeler et al., Mitotic Inhibition and Chromosome Displacement Induced by Estradiol in Chinese Hamsters Cells, *Cell Motility and the Cytoskeleton*, vol./Iss: 7 (3), pp. 235–247, 1987.

Yue et al., 2–Methoxyestradiol, an Edogenous Estrogen Metabolite, Induces Apoptosis in Endothelial Cells and Inhibits Angiogenesis: Possible Role for Stress–Activated Protein Kinase Signaling Pathway and Fas Express, *Molecular Pharmacology*, vol./Iss: 51, pp. 951–952, 1997.

Arnoldi et al., Sweet Isovanillyl Derivatives: Synthesis and Structure–Taste Relationships of Conformationally Restricted Analogs (abstract only), *Journal of Agric. Food Chem.* vol./Iss: 46(10), pp. 4002–1010, 1998.

Audier et al., Orientation de la fragmentation en spectrometrie de masse par introduction de groupements fonctionnels. VII.—Etheylenecetals de ceto–2 steroides, *Bulletin De La Societe Chimique De France*, vol./Iss: 10, pp. 3088–3090, 1965.

Cambie et al., Aromatic Steroids. Part II. Chromium Trioxide Oxidation of Some Oestra–1,3–5(10)–trienes, *Journal of the Chemical Society*, vol./Iss: 9, pp. 1234–1240, 1969.

Fetizon et al., Synthesis of 2–keto steroids (abstract only), *Bull. Soc. Chim. FR.*, vol./Iss: 8, pp. 3301–3306, 1968.

Lichtenauer et al., Zur Behandlung des Prostata–Karzinoms, *Deutsches medizinisches Journal*, vol./Iss: 23, pp. 248–249, Jan. 1972.

Limantsev et al., Effect of some estrogen structural analogs on the development of the mouse embyo (abstract only), *Akush Jinekol.*, vol./Iss: 6, pp. 55–56, 1982.

Miller, Thomas, Tubulin as a Therapeutic Target (Abstract only), *Dissertations Abstracts International*, vol./Iss: 5907B, pp. 3454, 1998.

Numazawa et al., Efficient Synthesis of 2–Methoxy– and 4–Methoxy–Estrogens, *Journal of the Chemical Society*, pp. 533–534, Jan. 10, 1983.

Rao et al., Structural Specificity of Estrogens in the Induction of Mitotic Chromatid Non–Disjunction in Hela Cells, *Experimental Cell Research*, vol./Iss: 48 pp. 71–81, 1967.

Rao et al., A Novel, Two–Step Synthesis of 2–Methoxyestradiol, *Synthesis*, pp. 168–169, Mar. 1, 1977.

Sakakibara, Kyoichi, 2–Hydroxy–1,3,5(10)–estratriene derivatives (abstract only) Identifier. XP–00218126, *Chemical Abstracts*, vol./Iss: 60(1), Jan. 6, 1964.

Aboulwafa et al., Synthesis and evaluation for uterotrophic and antiimplantation activities of 2–substituted estradiol derivatives, *Steroids*, vol./Iss: 57, pp. 199–204, Apr. 1992.

Blickenstaff et al., Synthesis of Some Analogs of Estradiol, *Steroids*, vol./Iss: 46 (4,5), pp. 889–902, Oct. 1985.

Brandi et al., Bone endothelial cells as estrogen targets (Abstract only), *Calcif. Tissue Int.*, vol./Iss: 53 (5), pp. 312–317, 1993.

Brueggemeier et al., 2–Methoxymethylestradiol: a new 2–methoxy estrogen analog that exhibits antiproliferative activity and alters tubulin dynamics, *Journal of Steroid Biochemistry & Molecular Biology*, vol./Iss: 78, pp. 145–156, 2001.

Crabbe, P., Cotton effect of the styrene chromophore (Abstract only), *Chem. Ind.*, vol./Iss: 27, pp. 917–918, 1969.

Dubey et al., Methoxyestradiosl Mediate the Antimitogenic Effects of Estradiol on Vascular Smooth Muscle Cells via Estrogen Receptor–Independent Mechanisms, *Biochemical and Biophysical Research Communications*, vol./Iss: 278, pp.27–33, 2000.

El–Tombary, Synthesis, Uterotropic, And Antiuterotrophic Activities of Some Estradiol Derivatives Containing Thiadiazole, Thiazoline, and Thiazolidinone Moieties, *Arch. Pharm. Pharm. Med. Chem.*, vol./Iss: 330 (9–10), pp. 295–302, 1997.

Emons et al., Modulation der hypophysaren Skekretion von Luteinisierendem Hormon (LH) durch Ostrogene, *FOCUS MHL*, vol./Iss: 3, pp. 221–228, 1986.

Fanchenko et al., Characteristics of the guinea pig uterus estrogen receptor system (Abstract only), *Byull. Eksp. Biol. Med.*, vol./Iss: 85 (4), pp. 467–470, 1978.

Fraser et al., Angiogenesis and its control in the female reproductive system (Abstract only), *British Medical Bulletin*, vol./Iss: 56 (3), pp. 787–797, 2000.

Gandhi et al., Mannich reaction of estrone, *Journal of Indian Chem. Soc.*, vol./Iss: 39, pp. 306–308, 1962.

Hahnel et al., The Specificity of the Estrogen Receptor of Human Uterus, *Journal of Steroid Biochemistry*, vol./Iss: 4, pp. 21–31, 1973.

He et al., Novel Cytokine Release Inhibitors. Part II: Steroids, *Bioorganic & Medicinal Chemistry Letters*, vol./Iss: 8, pp. 2825–2828, 1998.

Hejaz et al., Synthesis and Biological Activity of the Superestrogen (E)–17–Oximino–3–O–sulfamoyl–1,3,5(10)–estratriene: X–ray Crystal Structure of (E)–17–Oximino–3–hydroxy–1,3,5(10)–estratriene, *Journal of Medicinal Chemistry*, vol./Iss: 42 (16), pp. 3188–3192. 1999.

Holker et al., The Reactions of Estrogens with Benzeneseleninic Anhydride and Hexamethyldisilazane, *J. Chem. Soc. Perkin Trans.*, vol./Iss: I, pp. 1915–1918, 1982.

Hu, G., Neomycin inhibits angiogenin–induced angiogenesis (Abstract only), *Proceedings of the National Academy of Sciences, USA*, vol./Iss: 95 (17), pp. 9791–9795, 1998.

Ikegawa et al., Immunoaffinity extraction for liquid chromatographic determination of equilin and its metabolites in plasma (Abstract only), *Biomed. Chromatogr.*, vol./Iss: 10 (2), pp. 73–77, 1996.

Iriarte et al., Steroids (XCIV). Synthesis of 2–methyl and 1,2–dimethyl estrogens (Abstract only), *Tetrahedron*, vol./Iss: 3, pp. 28–36, 1958.

Jaggers et al., Potent Inhibitory effects of steroids in an in vitro model of angiogenesis (Abstract only), *Journal of Endocrinology*, vol./Iss: 150 (3), pp. 457–464, 1996.

Kovacs et al., Steroids. XXIII. Synthesis of 2– and 4–hydroxy and 2,4–dihydroxy derivatives of estrone and estradiol (Abstract only), *Acta Phys.Chem.*, vol./Iss: 19 (3), pp. 287–290, 1973.

Kurebayashi et al., Paradoxical hormone responses KPL–1 breast cancer cells in vivo: a significant role of angiogenesis in tumor growth (Abstract only), *Oncology*, vol./Iss: 59 (2), pp. 158–165, 2000.

Lippert et al., The effect of A–ring and D–ring metabolites of estradiol on the proliferation of vascular endothelial cells, *Life Sciences*, vol./Iss: 67, pp. 1653–1658, 2000.

Loozen et al., An approach to the synthesis of 7.beta–amino estrogens (Abstract only), *Recl: J.R. Neth.Chem. Soc.*, vol./Iss: 102 (10), pp. 433–437, 1983.

Lovely et al., 2–(Hydroxyalkyl)estradiols:Synthesis and Biological Evaluation, *Journal of Medicinal Chemistry*, vol./Iss: 39, pp. 1917–1923, 1996.

MacCarthy–Morrogh et al., Differential Effects of Estrone and Estrone–3–O–Sulfamate Derivatives on Mitotic Arrest, Apoptosis, and Microtubule Assembly in Human Breast Cancer Cells, *Cancer Research*, vol./Iss: 60, pp. 5441–5450, Oct. 1, 2000.

Michel et al., Inhibition of synaptosomal high–affinity uptake of dopamine and serotonin by estrogen agonists and antagonists (Abstract only), *Biochem. Pharmacol.*, vol./Iss: 36 (19), pp. 3175–3180, 1987.

Morisaki et al., Steroids. LI. Aromatization reaction of the cross–conjugated dienone system by Zinc 9. (Abstract only), *Chem. Pharm. Bull.*, vol./Iss: 14 (8) pp. 866–872, 1966.

Mueck et al., Angiogenetic and anti–angiogenetic effects of estradiol and its metabolites (Abstract only), *Journal of Clinical and Basic Cardiology*, vol./Iss: 4 (2), pp. 153–155, 2001.

Nambara et al., Microbial transformation products derived from steriods. I. Synthesis of 1,2– and 3–dimethoxy–4–methylestratrienes (Abstract only), *Chem. Pharm. Bull.*, vol./Iss: 20 (2), pp. 336–342, 1972.

Numazawa et al., Novel and Regiospecific Synthesis of 2–Amino Estrogens via Zincke Nitration, *Steroids*, vol./Iss: 41 (5), pp. 675–682, 1983.

Omar et al., Synthesis, binding affinities and uterotrophic activity of some 2–substituted estradiol and ring–A–fused pyrone derivatives, *European Journal of Medicinal Chemistry*, vol./Iss: 29, pp. 25–32, 1994.

Pert et al., Preparations of 2,4–disubstituted estradiols (Abstract only), *Australian Journal of Chemistry*, vol./Iss: 42 (3), pp. 421–432, 1989.

Peters et al., 17–Desoxy Estrogen Analogues, *Journal of Medicinal Chemistry*, vol./Iss: 32 (7), pp. 1642–1652, 1989.

Pfeiffer et al., Are catechol estrogens obligatory mediators of estrogen action in the central nervous system? I. Characterization of pharmacological probes with different receptor binding affinities and catechol estrogen formation rates (Abstract only), *Journal of Endocrinology*, vol./Iss: 110 (3), pp. 489–497, 1986.

Sato et al., Natural estrogens induce modulation of microtubules in Chinese hamster V79 cells in culture (Abstract only), *Horm. Carinog. II. Proceedings Int. Symp., 2nd (1996), Meeting Date 1994*, pp. 454–457, 1996.

Shishkina et al., Synthesis and properties of condensed heterocyclic derivatives of estra–4, 9–dien–17.beta.–o1–3–one (Abstract only), *Khim.–Farm. Zh.*, vol./Iss: 8 (1), pp. 7–11, 1974.

Singh et al., Inhibition of deoxyglucose uptake in MCF-7 breast cancer cells by 2–methoxyestrone and 2–methoxyestrone–3–O–sulfamate (Abstract only), *Molecular and Cellular Endocrinology*, vol./Iss: 160 (1–2), pp. 61–66, 2000.

Siracus et al., The effect of microtubule– and microfilament– disrupting drugs on preimplantation mouse embryos (Abstract only), *Journal of Embryology and Experimental Morphology*, vol./Iss: 60, pp. 71–82, Dec. 1980.

Spyriounis et al., Copper (II) complex of an estradiol derivative with potent antiinflammatory properties (Abstract only), *Arch. Pharm.*, vol./Iss: 324 (9), pp. 533–536, 1991.

Wang et al., Photoaffinity labeling of human placental estradiol 17.beta.dehydrogenase with 2– and 4–azidoestrone, 2– and 4–azidoestradiol (Abstract only), *Shengwu Huaxue Zazhi*, vol./Iss: 8 (6), pp. 715–718, 1992.

Wang et al., Synthesis of B–Ring Homologated Estradiol Analogues that Modulate Tubulin Polymerization and Microtubule Stability, *Journal of Medicinal Chemistry*, vol./Iss: 43, pp. 2419–2429, 2000.

Wiese et al., Induction of the Estrogen Specific Mitogenic Response of MCF–7 Cells by Selected Analogues of Estradiol–17β. A 3D QSAR Study, *Journal of Medicinal Chemistry*, vol./Iss: 40, pp. 3659–3669, 1997.

Wurtz et al., Three–Dimensional Models of Estrogen Receptor Ligand Binding Domain Complexes, Based on Related Crystal Structures and Mutational and Structure–Activity Relationsip Data, *Journal of Medicinal Chemistry*, vol./Iss: 41, pp. 1803–1814, 1998.

2–Methoxyestradiol—An Orally Active Endogenous Inhibitor of Angiogencis, *EntreMed Website Article*, pp. 1–10, Jul. 11, 2000.

Romanelli et al., Ethyl–p–Dimethylaminophenylacetate, *Organic Synthesis*, vol./Iss: 5, pp. 552, Oct. 24, 1973.

Yasuda et al., Accelerated differentiation in seminiferous tubules of fetal mice prenatally exposed to ethinayl estradiol (Abstract only), *Anat. Embryol. (Berl.)*, vol./Iss: 174 (3), pp. 289–299, 1986.

* cited by examiner

Fig. 1

ANTIANGIOGENIC AGENTS

CROSS REFERENCE TO RELATED APPLICATION

This application is a continuation of, and claims priority to, U.S. application Ser. No. 09/641,327, filed Aug. 18, 2000.

FIELD OF THE INVENTION

The present invention relates to treating disease states characterized by abnormal cell mitosis and or abnormal angiogenesis. More particularly, the present invention relates to certain analogs of 2-methoxyestradiol (2ME2) and their effect on diseases characterized by abnormal cell mitosis and/or abnormal angiogenesis.

BACKGROUND OF THE INVENTION

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, *Herpes simplex* infections, *Herpes zoster* infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several kinds of compounds have been used to prevent angiogenesis. Taylor et al. have used protamine to inhibit angiogenesis, see Taylor et al., *Nature* 297:307 (1982). The toxicity of protamine limits its practical use as a therapeutic. Folkman et al. have disclosed the use of heparin and steroids to control angiogenesis. See Folkman et al., *Science* 221:719 (1983) and U.S. Pat. Nos. 5,001,116 and 4,994,443. Steroids, such as tetrahydrocortisol, which lack gluco and mineral corticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors such as interferon inhibit angiogenesis. For example, interferon α or human interferon β has been shown to inhibit tumor-induced angiogenesis in mouse dermis stimulated by human neoplastic cells. Interferon β is also a potent inhibitor of angiogenesis induced by allogeneic spleen cells. See Sidky et al., *Cancer Research* 47:5155–5161 (1987). Human recombinant α interferon (alpha/A) was reported to be successfully used in the treatment of pulmonary hemangiomatosis, an angiogenesis-induced disease. See White et al., *New England J. Med.* 320:1197–1200 (1989).

Other agents which have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A1. Folkman et al., described several proteins derived from endogenous proteins including angiostatin and endostatin. (See, for example, U.S. Pat. Nos. 6,024,688 and U.S. Pat. No. 5,854,205 which are incorporated in their entirety) D'Amato et al., described 2-methoxyestradiol and derivatives of 2-methoxyestradiol in U.S. Pat. Nos. 5,504,074 and 5,661,143 which are incorporated herein by reference entirety.

The above compounds are either topical or injectable therapeutics. Therefore, there are drawbacks to their use as a general angiogenic inhibitor and lack adequate potency. For example, in prevention of excessive wound healing, surgery on internal body organs involves incisions in various structures contained within the body cavities. These wounds are not accessible to local applications of angiogenic inhibitors. Local delivery systems also involve frequent dressings which are impracticable for internal wounds, and increase the risk of infection or damage to delicate granulation tissue for surface wounds.

Thus, a method and composition are needed that are capable of inhibiting angiogenesis and which are easily administered. A simple and efficacious method of treatment would be through the oral route. If an angiogenic inhibitor could be given by an oral route, the many kinds of diseases discussed above, and other angiogenic dependent pathologies, could be treated easily. The optimal dosage could be distributed in a form that the patient could self-administer.

Other diseases are also characterized by an abnormal balance between cellular mitosis and apoptosis. One of these diseases is osteoporosis. Osteoporosis is characterized by a reduction in the bone mass of the skeleton which leads to skeletal fragility and an increased risk of fracture. In humans, the most common sites of fracture are found in the forearm, the vertebrae and the hip bones. Osteoporosis and its attendant fractures are a major cause of morbidity and mortality and lead to increased health costs for care.

In treating osteoporosis the main objective is to prevent fractures by stopping the loss of skeletal integrity. A variety of different therapies have been tried to achieve this objective, such as calcium, Vitamin D supplements and hormone replacement. Calcitonin has been used to improve bone mineral density at all bone sites. Bisphosphonates are an important group of therapeutic agents used for treatment of osteoporosis. They act by inhibiting bone resorption and increase bone density. Cyclical etidronate treatment aids in decreasing vertebral fractures, as does hormone replacement therapy and calcitonin. Alendronate has been shown to decrease the risk of symptomatic fractures of the forearm, spine and hip.

None of these treatments have proven to be effective in large numbers of osteoporotic patients. Additionally, the currently used therapies have unwanted side effects that create compliance and tolerance problems in treatment regimens. The most common adverse events with cyclical etidronate and alendronate are gastrointestinal disturbances. Esophagitis has also been a complication of therapies with alendronate. Cyclical etidronate has been shown to lead to focal osteomalacia. Hormone replacement therapies lead to estrogen effects such as uterine hypertrophy, and a potential for stimulation of estrogen-sensitive tumors leading to complications such as breast cancer.

What is needed are safe and effective treatments that do not create unwanted side effects.

2-Methoxyestradiol is an endogenous metabolite of estradiol (E2) that has potent anti-proliferative activity and induces apoptosis in a wide variety of tumor and non-tumor cell lines. When administered orally, it exhibits anti-tumor and anti-proliferative activity with little or no toxicity. In vitro data suggests that 2-methoxyestradiol does not engage the estrogen receptor for its anti-proliferative activity and is not estrogenic over a wide range of concentrations, as accessed by estrogen dependant MCF-7 cell proliferation. However, the presence of demethylases in vivo may metabolize this compound to 2-hydroxyestradiol, which has been shown to be estrogenic by several approaches. What is needed is a means to improve the bioavailibility of estradiol or 2-methoxyestradiol and to reduce the formation of estrogenic 2-methoxyestradiol metabolities. What is also needed is a means to modify estradiol or 2-methoxyestradiol in such a way that the molecule can not be converted into an uterotropic derivative.

SUMMARY OF THE INVENTION

The present invention provides certain analogs of 2-methoxyestradiol that are effective in treating diseases characterized by abnormal mitosis and/or abnormal angiogenesis. Specifically the present invention relates to analogs of 2-methoxyestradiol that have been modified at the 2 position and the 16 position. Compounds within the general formulae that inhibit cell proliferation are preferred. Preferred compositions may also exhibit a change (increase or decrease) in estrogen receptor binding, improved absorption, transport (e.g. through blood-brain barrier and cellular membranes), biological stability, or decreased toxicity. The invention also provides compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

Since 2-methoxyestradiol is metabolized to a much less active metabolite, the present invention adds steric bulk and/or modification of electrostatic characteristics at position 16 of 2-methoxyestradiol for retarding or preventing interaction of 17β-hydroxysteroid dehydrogenases and co-factor $NADP^+$ on this substrate. Addition of steric bulk and/or modification of electrostatic characteristics at position 16 of 2-methoxyestradiol may retard or prevent glucuronidation. It is believed that retardation or prevention of these two metabolic deactivation pathways prolongs the serum lifetime of 2-methoxyestradiol and other estrogenic compounds while retaining the desired anti-angiogenic and anti-tumor activity.

Aside from preventing the possible metabolism of 2ME2 to 2ME1, which may occur by making these steroids poor substrates for 17B-HSD (by either steric and/or electronic effects), it is not possible for these analogs to undergo the demethylation known to occur with 2ME2 since there is no methyl ether group at that position. This is desirable since it has been demonstrated that 2-hydroxyestradiol (the product of demethylation of 2ME2) has estrogenic activity.

Also disclosed is a method for modifying the methyl ether of 2-methoxyestradiol so that it can not be a substrate for demethylase and the resulting compounds.

Other features and advantages of the invention will be apparent from the following description of preferred embodiments thereof.

DETAILED DESCRIPTION OF THE INVENTION

As described below, compounds that are useful in accordance with the invention include novel estradiol derivatives that exhibit anti-mitotic, anti-angiogenic and anti-tumor properties. Specific compounds according to the invention are described below. Preferred compounds of the invention are estradiol derivatives modified at either the 2 or 16 positions. Those skilled in the art will appreciate that the invention extends to other compounds within the formulae given in the claims below, having the described characteristics. These characteristics can be determined for each test compound using the assays detailed below and elsewhere in the literature.

Figure 1:
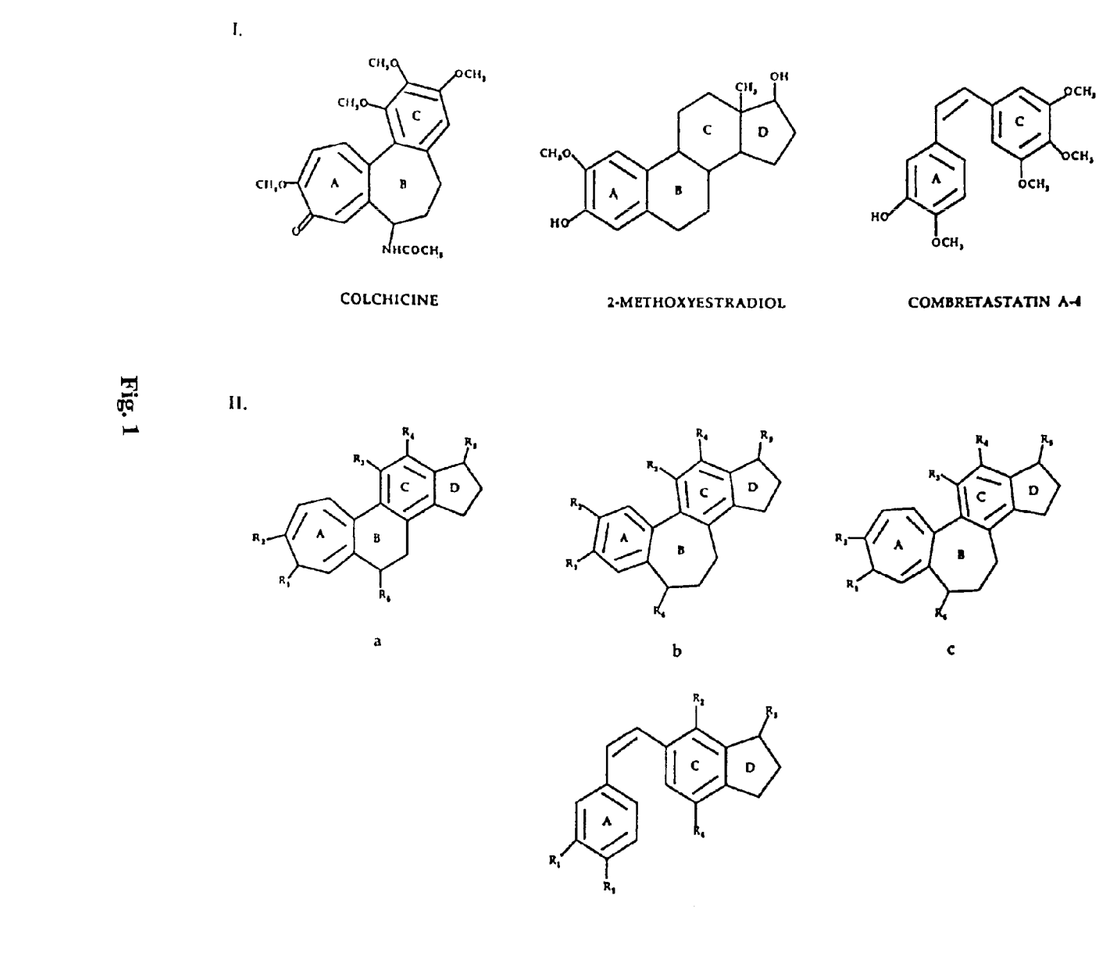
FIG. 1 depicts: I. colchicine, 2-methoxyestradiol and combretastatin A-4, and II. various estradiol derivatives comprising colchicine (a–c) or combretastatin A-4 (d) structural motifs as described below.

Without wishing to be bound to specific mechanisms or theory, it appears that certain compounds that are known to exhibit anti-mitotic properties such as colchicine and combretastatin A-4 share certain structural similarities with estradiol. FIG. 1 illustrates the molecular formulae of estradiol, colchicine, combretastatin A-4, and improved estradiol derivatives that exhibit anti-mitotic, anti-angiogenic and anti-tumor properties. Molecular formulae are drawn and oriented to emphasize structural similarities between the ring structures of colchicine, combretastatin A-4, estradiol, and certain estradiol derivatives. Estradiol derivatives are made by incorporating colchicine or combretastatin A-4 structural motifs into the steroidal backbone of estradiol.

FIG. 1, part I, depicts the chemical formulae of colchicine, 2-methoxyestradiol and combretastatin A-4. FIG. 1, part II a–d, illustrates estradiol derivatives that comprise structural motifs found in colchicine or combretastatin A-4. For example, part II a–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 1, may be fully saturated as found in 2-methoxyestradiol. $R_{1-6}$ represent a subset of the substitution groups found in the claims. Each $R_1$–$R_6$ can independently be defined as —$R_1$, $OR_1$, —$OCOR_{11}$—$SR_1$, —F, —$NHR_2$, —Br, —I, or —C≡CH.

2-Methoxyestradiol is an endogenous metabolite of estradiol that has potent anti-proliferative activity and induces apoptosis in a wide variety of tumor and non-tumor cell lines. When administered orally, it exhibits anti-tumor and anti-proliferative activity with little or no toxicity. 2-Methoxyestradiol is metabolized to a much less active metabolite, 2-methoxyestrone as indicated by in vitro and in vivo results. Although not wishing to be bound by theory, it is believed that this metabolite is formed through the same enzymatic pathway as estrone is formed from estradiol. Although not wishing to be bound by theory, it is believed that the enzymes responsible for this reversible reaction on estradiol are the 17β-hydroxysteroid dehydrogenases (17β-HSD) and NADP+ co-factor (Han et al., *J. Biol. Chem.* 275:2, 1105–1111 (Jan. 12, 2000) and other references cited earlier). Each of the four members of this enzyme family, types 1, 2, 3, and 4, have distinct activity. It appears that 17β-HSD type 1 catalyzes the reductive reaction (estrone to estradiol), while 17β-HSD type 2 catalyzes the oxidation reaction (estradiol to estrone), and type 3 catalyzes 4-androstenedione to testosterone. An additional metabolic deactivation pathway results in glucuronidation of 2-methoxyestradiol.

Since 2-methoxyestradiol is metabolized to a much less active metabolite, the present invention adds steric bulk and/or modification of electrostatic characteristics at position 16 of 2-methoxyestradiol for retarding or preventing interaction of the family of 17β-hydroxysteroid dehydrogenases and co-factor NADP+ on this substrate. Addition of steric bulk and/or modification of electrostatic characteristics at position 16 of 2-methoxyestradiol also retards or prevents glucuronidation. It is believed that retardation or prevention of these two metabolic deactivation pathways prolongs the serum lifetime of 2-methoxyestradiol and other estradiol derivatives while retaining the desired anti-angiogenic and anti-tumor activity.

Aside from preventing the possible metabolism of 2ME2 to 2ME1, which may occur by making these steroids poor substrates for 17B-HSD (by either steric and/or electronic effects), it is not possible for these analogs to undergo the demethylation known to occur with 2ME2 since there is no methyl ether group at that position. This is desirable since it has been demonstrated that 2-hydroxyestradiol (the product of demethylation of 2ME2) has estrogenic activity.

In another embodiment of the invention, estradiol derivatives are modified at the 2 position.

Anti-Proliferative Activity In Situ

Anti-proliferative activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Proliferative Activity In Vitro

The process by which $2ME_2$ affects cell growth remains unclear, however, a number of studies have implicated various mechanisms of action and cellular targets. $2ME_2$ induced changes in the levels and activities of various proteins involved in the progression of the cell cycle. These include cofactors of DNA replication and repair, e.g., proliferating cell nuclear antigen (PCNA) (Klauber, N., Parangi, S., Flynn, E., Hamel, E. and D'Amato, R. J. (1997), Inhibition of angiogenesis and breast cancer in mice by the microtubule inhibitors 2-methoxyestradiol and Taxol., Cancer Research 57, 81–86; Lottering, M-L., de Kock, M., Viljoen, T. C., Grobler, C. J. S. and Seegers, J. C. (1996) 17β-estradiol metabolites affect some regulators of the MCF-7 cell cycle. Cancer Letters 110, 181–186); cell division cycle kinases and regulators, e.g., $p34^{cdc2}$ and cyclin B (Lottering et al. (1996); Attalla, H., Mäkelä, T. P., Adlercreutz, H. and Andersson, L. C. (1996) 2-methoxyestradiol arrests cells in mitosis without depolymerizing tubulin. Biochemical and Biophysical Research Communications 228, 467–473; Zoubine, M. N., Weston, A. P., Johnson, D. C., Campbell, D. R. and Banjee, S. K. (1999) 2-Methoxyestradiol-induced growth suppression and lethality in estrogen-responsive MCF-7 cells may be mediated by down regulation of p34cdc2 and cyclin B1 expression. Int J Oncol 15, 639–646); transcription factor modulators, e.g., SAPK/JNK (Yue, T-L., Wang, X., Louden, C. S., Gupta, L. S., Pillarisetti, K., Gu, J-L., Hart, T. K., Lysko, P. G. and Feuerstein, G. Z. (1997) 2-methoxyestradiol, an endogenous estrogen metabolite induces apoptosis in endothelial cells and inhibits angiogenesis: Possible role for stress-activated protein kinase signaling pathway and fas expression. Molecular Pharmacology 51, 951–962; Attalla, H., Westberg, J. A., Andersson, L. C., Aldercreutz, H. and Makela, T. P. (1998) 2-Methoxyestradiol-induced phosphorylation of bcl-2: uncoupling from JNK/SAPK activation. Biochem and Biophys Res Commun 247, 616–619); and regulators of cell arrest and apoptosis, e.g., tubulin (D'Amato, R. J., Lin, C. M., Flynn, E., Folkman, J. and Hamel, E. (1994) 2-Methoxyestradiol, and endogenous mammalian metabolite, inhibits tubulin polymerization by interacting at the colchicine site. Proc. Natl. Acad. Sci. USA 91, 3964–3968; Hamel, E., Lin, C. M., Flynn, E. and D'Amato, R. J. (1996) Interactions of 2-methoxyestradiol, and endogenous mammalian metabolite, with unploymerized tubulin and with tubulin polymers. Biochemistry 35, 1304–1310), $p21^{WAF1/CIP1}$ (Mukhopadhyay, T. and Roth, J. A. (1997) Induction of apoptosis in human lung cancer cells after wild-type p53 activation by methoxyestradiol. Oncogene 14, 379–384), bcl-2 and FAS (Yue et al. (1997); Attalla et al. (1998)), and p53 (Kataoka, M., Schumacher, G., Cristiano, R. J., Atkinson, E. N., Roth, J. A. and Mukhopadhyay, T. (1998) An agent that increases tumor suppressor transgene product coupled with systemic transgene delivery inhibits growth of metastatic lung cancer in vivo. Cancer Res 58, 4761–4765; Mukhopadhyay et al. (1997); Seegers, J. C., Lottering, M-L., Grobler C. J. S., van Papendorp, D. H., Habbersett, R. C., Shou, Y. and Lehnert B. E. (1997) The mammalian metabolite, 2-methoxyestradiol, affects p53 levels and apoptosis induction in transformed cells but not in normal cells. J. Steroid Biochem. Molec. Biol. 62, 253–267). The effects on the level of cAMP, calmodulin activity and protein phosphorylation may also be related to each other. More recently, 2ME2 was shown to upregulate Death Receptor 5 and caspase 8 in human endothelial and tumor cell lines (LaVallee, T. M., Hembrough, W. A., Williams, M. S., Zhan, X. H., Pribluda, V. S., Papathanassiu, A., and Green, S. J. 2-Methoxyestradiol upregulates DR5 and induces apoptosis independently of p53. (Submitted for publication)). All cellular targets described above are not necessarily mutually exclusive to the inhibitory effects of $2ME_2$ in actively dividing cells.

The high affinity binding to SHBG has been mechanistically associated to its efficacy in a canine model of prostate cancer, in which signaling by estradiol and 5α-androstan-3α,17β-diol were inhibited by $2ME_2$ (Ding, V. D., Moller, D. E., Feeney, W. P., Didolkar, V., Nakhla, A. M., Rhodes, L., Rosner, W. and Smith, R. G. (1998) Sex hormone-binding globulin mediates prostate androgen receptor action via a novel signaling pathway. Endocrinology 139, 213–218).

The more relevant mechanism described above have been extensively discussed in Victor S. Pribluda, Theresa M. LaVallee and Shawn J. Green, 2-methoxyestradiol: *a novel endogenotis chemotherapeutic and antiangiogenic* in The New Angiotherapy, Tai-Ping Fan and Robert Auerbach eds., Human Press Publisher.

Assays relevant to the mechanisms of action and activity are well-known in the art. For example, anti-mitotic activity mediated by effects on tubulin polymerization activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture (all concentrations refer to a final reaction volume of 0.25 µl) contains 1.0M monosodium glutamate (pH 6.6), 1.0mg/ml (10 µM) tubulin, 1.0 mM $MgCl_2$, 4% (v/v) dimethylsulfoxide and 20–75 µM of a composition to be tested. The 0.24 ml reaction mixtures are incubated for 15 min. at 37° C. and then chilled on ice. After addition of 10 µl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 below.

Other such assays include counting of cells in tissue culture plates or assessment of cell number through metabolic assays or incorporation into DNA of labeled ($^3$H-thymidine) or immuno-reactive (BrdU) nucleotides. In addition, antiangiogenic activity may be evaluated through endothelial cell migration, endothelial cell tubule formation, or vessel outgrowth in ex-vivo models such as rat aortic rings.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofribomas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

In addition, the invention can be used to treat a variety of post-menapausal symptoms, including osteoporosis, cardiovascular disease, Alzheimer's disease, to reduce the incidence of strokes, and as an alternative to prior estrogen replacement therapies. The compounds of the present invention can work by estrogenic and non-estrogenic biochemical pathways.

Improved Estradiol Derivative Synthesis

Known compounds that are used in accordance with the invention and precursors to novel compounds according to the invention can be purchased, e.g., from Sigma Chemical Co., St. Louis, Steraloids and Research Plus. Other compounds according to the invention can be synthesized according to known methods from publicly available precursors.

The chemical synthesis of estradiol has been described (Eder, V. et al., *Ber* 109, 2948 (1976); Oppolzer, D. A. and Roberts, D. A. *Helv. Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedren* 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index,* 11th Ed., Merck & Co., Inc., Rahway, N.J. USA (1989), pp. 583–584).

Analogs of 2ME2 or 2-ethoxyestradiol containing 7 membered rings can be modified to include appropriate chemical side groups according to the invention by known chemical methods (see for example, Miller, T. A.; Bulman, A. L.; Thompson, C. D.; Garst, M. E.; Macdonald, T. L. "Synthesis and Structure-Activity Profiles of A-Homoestranes, the Estratropones." J. Med. Chem., 1997, 40, 3836–3841; Miller, T. A.; Bulman, A. L.; Thompson, C. D.; Garst, M. E.; Macdonald, T. L. "The Synthesis and Evaluation of Functionalized Estratropones-Potent Inhibitors of Tubulin Polymerization." Bioorg. Med. Chem. Letters, 1997, 7, 1851–1856; and Wang, Z.; Yang, D.; Mohanakrishnan, A. K.; Fanwick, P. E.; Nampoothiri, P.; Hamel, E.; Cushman, M. "Synthesis of B-Ring Homologated Estradiol Analogs that Modulate Tubulin Polymerization and Microtubule Stability." J. Med. Chem., 2000, 43, 2419–2429. These articles do not utilize ring closure strategies to make the seven membered ring, rather they use a ring expansion strategy. The Cushman article explores B-Ring expanded analogs whereas the other articles deal with the expanded the A-ring.)

The synthetic pathways used to prepare the derivatives of the present invention are based on modified published literature procedures for estradiol derivatives and dimethylenamines (Trembley et al., *Bioorganic & Med. Chem.* 1995 3, 505–523; Fevig et al., *J. Org. Chem.,* 1987 52, 247–251; Gonzalez et al., *Steroids* 1982, 40, 171–187; Trembley et al., Synthetic Communications 1995, 25, 2483–2495; Newkome et al., J. Org. Chem. 1966, 31, 677–681; Corey et al Tetrahedron Lett 1976, 3–6; and Corey et al., Tetrahedron Lett, 1976, 3667–3668]. The modifications are provided in Example 1 below. Initial screening of epimeric 16-ethyl-2-methoxyestradiol and related analogues showed that it is about equipotent to 2-methoxyestradiol in inhibition of HUVEC cell proliferation in vitro.

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991). The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

2-Methoxyestradiol is an endogenous metabolite of estradiol (E2) that has potent anti-proliferative activity and induces apoptosis in a wide variety of tumor and non-tumor cell lines. When administered orally, it exhibits anti-tumor and anti-proliferative activity with little or no toxicity. In vitro data suggests that 2-methoxyestradiol does not engage the estrogen receptor for its anti-proliferative activity and is not estrogenic over a wide range of concentrations, as accessed by estrogen dependant MCF-7 cell proliferation. However, the presence of demethylases in vivo may metabolize this compound to 2-hydroxyestradiol, which has been shown to be estrogenic by several approaches. The present invention improves the bioavailibility of estradiol or 2-methoxyestradiol and to reduces the formation of estrogenic 2-methoxyestradiol metabolities. The present invention modifies estradiol or 2-methoxyestradiol in such a way that the molecule can not be converted into an uterotropic derivative.

One embodiment of the invention modifies the methyl ether of 2-methoxyestradiol so that it can not be a substrate for demethylase. Additionally, it has been demonstrated (Cushman et al *J. Med. Chem.* 1995, 38, 2041–2049) that other electron-rich groups at the 2-position of estradiol (propyne, propene, ethoxy) have good anti-proliferative activity in vitro. It is disclosed that modifications at C-2 of estradiol such as formyl, acetyl, methanol, 1-ethanol, 2-ethanol, amino, alkylamino, dialkyl amino, methyleneamine, methylene alkyl amine and methylene dialkylamine, and alkyl amide are be anti-proliferative and anti-angiogenic agents have reduced or removed uterotropic activity. Alkyl is defined as any carbon chain up to 6 carbons in length that is branched or straight. Listed below in Table 1 are data of 2-modified estradiol derivatives in HUVEC, MDA-MB-231 and MCF7 proliferation data. The synthetic paths for preparation of these analogs can be found in Pert et al *Aust. J. Chem.* 1989, 42, 405–419. Lovely et al *Tetrahedron Lett.* 1994, 35, 8735–8738. Gonzalez et al *Steroids* 1982, 40, 171–187. Nambara et al *Chem. Pharm. Bull.* 1970, 18, 474–480. Cushman et al *J. Med. Chem.* 1995, 38, 2041–2049 and methods developed in-house and are discussed below.

TABLE 1

| Compound | HUVEC (IC$_{50}$ μM) | MDA-MB-231 (IC$_{50}$ μM) | MCF7 Proliferation Index |
|---|---|---|---|
| E2 | NA | NA | 13.1 |
| 2ME2 | 0.5 | 0.9 | 4.4 |
| 2-methyl hydroxy-E2 | 10 | >25 | 7.4 |
| 2-formyl-E2 | 8 | >25 | 5.4 |
| 2-acetyl-E2 | 18 | 9 | 4.4 |

All of the 2-modified analogs presented in Table 1 have significantly less estrogenic activity (compared to estradiol) as represented by their proliferation index in estrogen dependant MCF-7 cells. All of these analogs have the capacity to from a hydrogen bond with the hydroxy group at position 3 and this may be the reason for their relatively low estrogenic character compared to estradiol. Both the 2-methylhydroxy and 2-formyl derivatives had good antiproliferative activity (IC50<10 microM) in HUVEC cells, whereas the 2-acetyl had poor activity in the same assay. In contrast, 2-methylhydroxy and 2-formyl were inactive in breast tumor MDA-MB-231 cells while 2-acetyl E2 had good activity in this cell line.

Although not wishing to be bound by theory, molecular modeling suggests that there may be a hydrogen bond that forms between the 3-hydroxy group and the methoxy group of 2-methoxyestradiol. This interaction may be important for both 2-methoxyestradiol's anti-proliferative and anti-angiogenic action as well as its non-estrogenic activity. It is claimed that any group that can be placed at position 2 of estradiol and has the potential to form a hydrogen bond with the 3-hydroxy group is an anti-proliferative and anti-angiogenic agent that lacks estrogenic activity.

It should be understood that in addition to the ingredients, particularly mentioned above, the formulations of this invention may include other agents convention in the art having regard to the type of formulation in question, for example, those suitable for oral administration may include flavoring agents.

EXPERIMENTAL DATA

The following Examples refer to the compound of the general formula:

wherein:

a) $R_b$ and $R_o$ are independently —H, —Cl, —Br, —I, —F, —CN, lower alkyl, —OH, —CH$_2$—OH, —NH$_2$; or N(R$_6$)(R$_7$), wherein R$_6$ and R$_7$ are independently hydrogen or an alkyl or branched alkyl with up to 6 carbons;

b) $R_a$ is —N$_3$, —C≡N, —C≡C—R, —CH=CH—R, —R—CH=CH$_2$, —C≡CH, —O—R, —R—R$_1$ —OC(O)CH$_3$, —C(O)H, —NH$_2$, —NMe$_2$, —NHMe, or —O—R—R$_1$ where R is a straight or branched alkyl with up to 10 carbons or aralkyl, and R$_1$ is —OH, —NH$_2$, —Cl, —Br, —I, —F or CF$_3$;

c) Z' is >CH, >COH, or >C—R$_2$—OH, where R$_2$ is an alkyl or branched alkyl with up to 10 carbons or aralkyl;

d) >C—R$_g$ is >CH$_2$, >C(H)—OH, >C=O, >C=N—OH, >C(R$_3$)OH, >C=N—OR$_3$, >C(H)—NH$_2$, >C(H)—NHR$_3$, >C(H)—NR$_3$R$_4$, or >C(H)—C(O)—R$_3$, where each R$_3$ and R$_4$ is independently an alkyl or branched alkyl with up to 10 carbons or aralkyl;

e) $R_{h1}$ and $R_{h2}$ are independently H, or a straight or branched chain alkyl, alkenyl or alkynyl with up to 6 carbons that is unsubstituted, or substituted with one or more groups selected from a hetero functionality (O—Y, N—Y$_2$ or S—Y) where Y is independently selected from H, Me or an alkyl chain up to 6 carbons; a halo functionality (F, Cl, Br or I); an aromatic group optionally substituted with hetero, halo or alkyl; or $R_{h1}$ and $R_{h2}$ are independently an aromatic group optionally substituted with hetero, halo or alkyl, provided that both $R_{h1}$ and $R_{h2}$ are not H;

f) Z" is >CH$_2$, >C=O, >C(H)—OH, >C=N—OR$_5$, >C(H)—C≡N, or >C(H)—NR$_5$R$_5$, wherein each R$_5$ is independently hydrogen, an alkyl or branched alkyl with up to 10 carbons or aralkyl;

and wherein all monosubstituted substituents have either an α or β configuration.

Lower alkyl is defined as a small carbon chain having 1–8 carbon atoms. The chain may be branched or unbranched.

EXAMPLE 1

Synthesis of 2-ME Derivatives and Modifications at the 16 Position

Synthesis of the 2-ME derivatives described herein is within the capability of one ordinarily skilled in the art. A specific description of the synthesis of the 2-ME derivatives having modifications at the 2 and 6 positions and analogs discussed herein can be found in M. Cushman, H-M. He, J. A. Katzenellenbogen, C. M. Lin and E. Hamel, Synthesis, antitubulin and antimitotic activity, and cytotoxicity of 2-methoxyestradiol, and endogenous mammalian metabolite of estradiol that inhibits tubulin polymerization by binding to the colchicine binding site, *J. Med. Chem.*, 38(12): 2042 (1995); and M. Cushman, H-M. He, J. Katzenellenbogen, R.

Varma, E. Hamel, C. Lin, S. Ram and Y. P. Sachdeva, Synthesis of analogs of 2-methoxyestradiol with enhanced inhibitory effects on tubulin polymerization and cancer cell growth, *J. Med. Chem.* 40(15): 2323 (1997).

The synthetic pathways used to prepare the derivatives of the estradiol derivatives modified at the 16 position of the present invention are based on modified published literature procedures for estradiol derivatives cited earlier. Examples of the modifications are provided in Examples 2 through 23 below.

EXAMPLE 2

Preparation of 3-Benzyl-2-methoxyestradiol

2-Methoxyestradiol (10.09 g, 33.4 mmol) and potassium carbonate (22 g, 278 mmol) were suspended in anhydrous ethanol and cooled to 0° C. Benzyl bromide (11.4 mL, 95.8 mmol) was added dropwise, and following the addition, the mixture was brought to reflux for 8 h. The solution was cooled to room temperature (rt), and the solvent was removed via rotoevap. The resulting residue was diluted with approximately 200 ml water, and washed with ethyl acetate (3×200 mL). The combined organics were washed with water (200 mL), sodium bicarbonate (saturated (satd), 200 mL) and brine (200 mL). Dry with sodium sulfate, filter and roto-evaporation (rotoevap). Product was dried under vacuo with occasional gentle heating using a heat gun to give a yellowish glass (13.54 g, quanitative yield) and used without further purification.

Selected spectral data: $^1$H-MNR (300 MHz, CDCl$_3$) δ 7.29–7.53 (m, 5H), 6.88 (s, 1H), 6.65 (s, 3H), 5.11 (s, 2H), 3.87 (s, 3H), 3.7 (t, J=8 Hz, 1H), 0.80 (s, 3H). FT-IR (neat) 3341, 2920, 2864, 1605, 1513, 1453, 1254, 1211, 1117, 1022 cm$^{-1}$.

EXAMPLE 3

Preparation of 3-Benzyl-2-methoxyestrone

Oxalyl chloride (38 mmol, 19 mL, 2M, methylene chloride) was added to anhydrous methylene chloride (25 mL) and cooled to −46° C. Methyl sulfoxide (5.40 mL, 76 mmol) was added dropwise, and the mixture was stirred for 2 minutes. 3-Benzyl-2-methoxyestradiol in methylene chloride/methyl sulfoxide (10 mL/15 mL) and added within 5 minutes and the resulting mixture was stirred for 1 h. Triethyl amine (170 mmol, 23.5 mL) was added drop-wise, stirred 5 minutes and warmed to rt. Water (~200 mL) was added and the mixture was washed with methylene chloride (3×200 mL). The combined organics were washed with water (200 mL), dilute HCl (1% aq., 200 mL), sodium carbonate (satd, 200 mL) and brine (200 mL). The organics were dried with magnesium sulfate, filtered and rotoevaped to give a white solid. The solid was crystallized with hot ethanol to give white crystals (9.94 g, 25.5 mmol, 76% overall yield from 2-methoxyestradiol).

Selected spectral data: $^1$H-NMR (300 MHz, CDCl$_3$) δ 7.28–7.48 (m, 5H), 6.86 (s, 1H), 6.66 (s, 1H), 3.88 (s, 3H), 0.94 (s, 3H). IR (neat) 2920, 1731, 1519, 1202, 1012 cm$^{-1}$.

EXAMPLE 4

Representative Preparation of 16α-alkyl-3-benzyl-2-methoxyestrone

Lithium diisopropyl amide (2M, Aldrich, heptane/THF/ ethylbenzene) was dissolved in THF and cooled to −78° C., and 3-benzyl-2-methoxyestrone in THF (10 mL) was added dropwise. Following addition, the mixture was warmed to 0° C. and stirred 1 hour (h). The mixture was then cooled to −78° C. and DMPU (1 mL) followed by crotyl bromide (205 μL, 2.0 mmol) were added dropwise. The mixture was warmed to rt over 4 h. The reaction was quenched by carefully adding water (100 mL) and washing with ethyl acetate (2×100 mL). The combined organics were washed with water (100 mL) and brine (100 mL). The solution was dried with magnesium sulfate, filtered and rotoevaped. The crude product was purified using hexane/ethyl acetate (9:1) SiO$_2$ Biotage FLASH apparatus. 680 mg (1.53 mmol) of product was obtained and approximately 121 mg (0.31 mmol) of starting material was recovered (90% yield based on recovered starting material). Diastereomeric ratio of 16 α/β is approximately 2:1 (s H18 signals at 0.88, 0.79 ppm).

Selected spectral data: $^1$H-MNR (300 MHz, CDCl$_3$) δ 7.28–7.48 (m, 5H), 6.86 (s, 1H), 6.66 (s, 1H), 5.34–5.59 (m, 2H), 5.13 (s, 2H), 3.88 (s, 3H), 0.87 & 0.97 (s, total 3H, ratio 1:2).

EXAMPLE 5

Representative Preparation of 16β-alkyl-3-benzyl-2-methoxyestrone

3-Benzyl-2-methoxyestrone (1.175 g, 3.0 mmol) was dissolved in anhydrous THF (15 mL), cooled to −78° C. and lithium diisopropyl amide (2M Aldrich, heptane/THF/ ethylbenzene) was added dropwise and stirred 1 h. DMPU (1 mL) followed by crotyl bromide (302 μL) were added and the mixture warmed to rt over 24 h. Workup as above and purify using hexane:ethyl acetate (4:1) SiO$_2$ flash column gave 492 mg purified product (1.1 mol, 37% yield).

Selected spectral data: $^1$H-MNR (300 MHz, CDCl$_3$) δ 7.28–7.48 (m, 5H), 6.86 (s, 1H), 6.66 (s, 1H), 5.62–5.34 (m, 2H), 5.13 (s, 2H), 3.89 (s, 3H), 0.98 and 0.87 (s, 3H total, ratio 2:1). IR (neat) 2928, 2854, 1732, 1606, 1508, 1452, 1215, 1016 cm$^{-1}$.

EXAMPLE 6

Representative Preparation of 16β-alkyl-3-benzyl-2-methoxyestrone 3-benzyl-16-carbomethoxy-2-methoxyestrone (0.840 g, 1.87 mmol), potassium hydride (1.5 g, 10.9 mmol, 30% mineral oil dispursion, washed in hexanes) and 18-crown-6 (120 mg, 0.4 mmol) was mixed in THF (40 mL) and refluxed for 1 h. The mixture was cooled to rt, and allyl bromide (537 μL, 6.2 mmol) was added and the mixture was refluxed for 18 h. After cooling to rt, the reaction was quenched by carefully adding approximately 2 ml of water with stirring, then adding an additional 100 mL water. This mixture was washed with ethyl acetate (2×100 mL) and the combined organics were washed with brine (100 mL). The organics were dried with magnesium sulfate, filtered and rotoevaped. Purification using 85:5 hexanes:ethyl acetate SiO$_2$ Biotage FLASH apparatus yielded 697 mg of product (1.42 mol, 76% yield).

Selected spectral data: $^1$H-MNR (300 MHz, CDCl$_3$) δ 7.28–7.48 (m, 5H), 6.85 (s, 1H), 6.66 (s, 1H), 566–5.79 (m, 1H), 5.15–5.20 (m, 2H), 5.13 (s, 2H), 3.88 (s, 3H), 3.75 (s, 3H), 0.99 (s, 3H).

EXAMPLE 7

Representative Decarboxylation of 16-alkyl-16-carbomethoxy-3-benzyl-2-methoxyestrone 16-allyl-16-carbomethoxy-3-benzyl-2-methoxyestrone (697 mg, 1.42 mmol), lithium chloride (1.15 g, 27 mmol), water (485 µL, 27 mmol) were dissolved in DMF (63 mL) and refluxed for 20 h. Cool to rt, add 1N HCl (100 mL) and wash with ether (2×100 mL) the combined organics were washed with water (100 mL), and brine 100 mL), dry with magnesium sulfate, filter and rotoevap. Purification by 85:15 hexanes:ethyl acetate $SiO_2$ Biotage Flash apparatus gave 271 mg product and 189 mg recovered starting material. Starting material was resubjected to the reaction (308 mg LiCl, 132 µL, water, 17 mL DMF) for 28 h and worked up as above to give 130 mg product. Overall yield for reaction was 66% (401 mg, 0.93 mmol).

Selected spectral data: $^1$H-NMR (300 MHz, $CDCl_3$) δ 7.28–7.48 (m, 5H), 6.85 (s, 1H), 6.65 (s, 1H), 5.69–5.88 (m, 1H), 5.13 (s, 2H), 5.00–5.08 (m, 2H), 5.88 (s, 3H), 0.98 nd 0.88 (s, total 3H, ratio 1:1.4). FT-IR (neat), 2925, 2855, 1726, 1514, 1214, 1103 $cm^{-1}$.

EXAMPLE 8

Preparation of 16-methane-dimethylenamine-3-benzyl-2-methoxyestrone 3-benzyl-2-methoxyestrone (1.51 g, 3.87 mmol) was suspended in tert-butoxy bis(dimethylamino)methane (1.64 mL, 8.13 mmol) and heated in an oil bath (155° C.) for 1.5 h, during which time the steroid dissolved. The reaction mixture was cooled to rt, and poured into ice water (100 mL) and washed with methylene chloride (2×100 mL). The organics were washed with brine (100 mL) dried with magnesium sulfate, filtered and rotoevaped to give product which was used without further purification (1.82 g, quantitative yield).

Selected spectral data: $^1$H-NMR (300 MHz, $CDCl_3$) δ 7.23–7.47 (m, 5H), 6.87 (s, 1H), 6.64 (s, 1H), 5.12 (s, 2H), 3.88 (s, 3H), 3.07 (s, 6H), 0.91 (s, 3H).

EXAMPLE 9

Preparation of 16-carbomethoxy-3-benzyl-2-methoxy estrone

3-Benzyl-2-methoxyestrone (1.6113 g, 2.978 mmol) was dissolved in THF (15 mL), cooled to −78° C. and lithium diisopropyl amide (2M, Aldrich, Heptane/THF/ethylbenzene) was added dropwise and stirred for 1 h. Methyl cyanoformate (237 µL, 3 mmol) in DMPU (1 mL) was added and the mixture warmed to rt over 18 h. Water (100 ml) was carefully added, and the mixture was washed with ethyl acetate (3×100 mL) and the combined organics were washed with brine (100 mL), dried with sodium sulfate, filtered and rotoevaped. Final purification of product using hexane:ethyl acetate (85:15) then switching to hexane:ethyl acetate (75:25) $SiO_2$ flash column yielded 806 mg product (1.8 mmol, 60%).

Selected spectral data: $^1$H-NMR (300 MHz, $CDCl_3$) δ 7.28–7.48 (m, 5H), 6.85 (s, 1H), 6.66 (s, 1H), 5.13 (s, 2H), 3.88 (s, 3H), 3.78 (s, 3H), 3.23 (dd, J=9, 10 Hz, 1H), 1.0 (s, 3H). FT-IR (neat) 2929, 2860, 1750, 1723, 1604, 1508, 1211, 1014 $cm^{-1}$.

EXAMPLE 10

Representative Procedure for Preparation of 16-alkyl-3-benzyl-2-methoxyestra-17β-diol 16α-crotyl-3-benzyl-2methoxyestrone (680 mg, 1.53 mmol) was dissolved in anhydrous THF (10 mL), and cooled to −78° C. Lithium aluminum hydride (3.06 mmol, 116 mg) was added and the solution was stirred for 2 h. The reaction was quenched by carefully adding water (2 mL) and warming to rt, then adding additional 50 mL portion of water. The mixture was washed with ethyl acetate (2×50 mL) and the combined organics were washed with water (50 mL), brine (50 mL), dried with magnesium sulfate, filtered and rotoevaped. The mixture was purified with 3:1 hexane:ethyl acetate $SiO_2$ Biotage FLASH apparatus to give 500 mg purified product (1.12 mmol, 73% yield).

Selected spectral data: $^1$H-NMR (300 MHz, $CDCl_3$) δ 7.28–7.48 (m, 5H), 6.87 (s, 1H), 6.64 (s, 1H), 5.47–5.56 (m, 2H), 5.12 (s, 2H), 3.88 (s, 3H), 3.8 (d, J=9 Hz) and 3.33 (d, J=8Hz) total 1H, ratio 1:1.7, 0.84 and 0.81 (s, 3H total).

EXAMPLE 11

Preparation of 16-methanol-3-benzyl-2-methoxyestradiol

Reaction procedure and work up as above, (used 806 mg, 1.8 mmol 16-carbomethoxy-3-benzyl-2-methoxyestrone), except warm to rt for 2 h before quenching. Purify final product with 3:2 hexane:ethyl acetate $SiO_2$ flash column. Obtain 304 mg β isomer, 51 mg α isomer which were separated by chromatography. Selected spectral data: $^1$H-NMR (300 MHz, $CDCl_3$) δ Major isomer 7.28–7.48 (m, 5H), 6.87 (s, 1H), 6.64 (s, 1H), 5.12 (s, 2H), 3.97 (d, J=10 Hz), 3.88 (s and obscured d, 4H), 3.67 (dd, J=4, 7 Hz, 1H), 0.87 (s, 3H). Minor isomer 7.28–7.47 (m, 5H), 6.86 (s, 1H), 6.64 (s, 1H), 3.88 (s, 3H), 3.83 (d, J=14 Hz, 1H), 3.69 (t, J=9 Hz, 1H), 3.54 (d, J=7 Hz, 1H), 0.87 (s, 3H).

EXAMPLE 12

Representative Debenzylation of 16-alkyl-3-benzyl-2-methoxyestradiol

16α-crotyl-3-benzyl-2-methoxyestradiol (500 mg, 1.12 mmol) was dissolved in ethyl acetate (25 mL) in Parr reaction bottle. The bottle was flushed with argon, and Pd/C (10%, 2.5 g) was added. The bottle was fitted to a Parr hydrogenator, filled and purged with hydrogen five times, pressurized to 50 psi, and agitated for 24 h. The mixture was filtered through a celite pad, rotoevaped and purified with a 3:1 hexane ethyl acetate $SiO_2$ flash column. Obtain 358 mg product (1.0 mmol, 89%).

Selected spectral data: $^1$H-NMR (300 MHz, $CDCl_3$) δ 6.81 (s, 1H), 6.66 (s, 1H), 3.87 (s, 3H), 3.76 (d, J=10 Hz) and 3.29 (d, J=8 Hz) (total 1H, ratio 1:2), 0.82 and 0.79 (s, 3H). FT-IR (neat) 3245, 2914, 1606, 1523, 1414, 1258, 1028 $cm^{-1}$. Analysis calculated (Anal. Calcd) for $C_{20}H_{34}O_3$: C, 77.44; H, 9.56. Found: C, 76.64; H, 9.51.

EXAMPLE 13

16β-methyl-2methoxyestradiol

Selected spectral data: $^1$H-NMR (300 MHz, $CDCl_3$) δ 6.81 (s, 1H), 6.66 (s, 1H), 3.87 (s, 3H), 3.73 (d, J=10 Hz) and 3.23 (d, J=8 Hz) (total 1H, 2:1), 0.83 and 0.81(s, 3 H total). Anal. Calcd for $C_{20}H_{28}O_3$, ¼ $H_2O$: C, 74.85; H, 8.95. Found: C, 74.93; H, 8.94.

EXAMPLE 14

16α-methyl-2methoxyestradiol

Selected spectral data: $^1$H-NMR (300 MHz, $CDCl_3$) δ 6.81 (s, 1H), 6.66 (s, 1H), 3.87 (s, 3H), 3.23 (d, J=7 Hz) (s, 1H), 0.81 (s, 3 H). Anal. Calcd for $C_{20}H_{28}O_3$, ¼ $H_2O$: C, 74.85; H, 8.95. Found: C, 74.98; H, 8.65.

EXAMPLE 15

Racemic 16-ethyl-2-methoxyestradiol

Selected spectral data: $^1$H-NMR (300 MHz, CDCl$_3$) δ 6.82 (s, 1H), 6.66 (s, 1H), 3.88 (s, 3H), 3.76 (d, J=9 Hz) and 3.30 (d, J=10 Hz), (1H total, ratio 1:1), 0.83 and 0.79 (s, 3H total). FT-IR (neat) 3214, 2918, 1605, 1522, 1229, 1201, 1024 cm$^{-1}$. Anal. Calcd for C$_{21}$H$_{30}$O$_3$: C, 76.33; H, 9.15. Found: C, 76.18; H, 9.16.

EXAMPLE 16

16α-n-propyl-2-methoxyestradiol

Selected spectral data: $^1$H-NMR (300 MHz, CDCl$_3$) δ 6.81 (s, 1H), 6.66 (s, 1H), 5.43 (s, 1H), 3.87 (s, 3H), 3.29 (t, J=7 Hz, 1H), 0.95 (t, J=7 Hz, 3H), 0.83 and 0.80 (s, total 3H, ratio 7.3:1). Anal. Calcd for C$_{22}$H$_{32}$O$_3$: C, 76.69; H, 9.37. Found: C, 76.55; H, 9.44.

EXAMPLE 17

16β-n-propyl-2-methoxyestradiol

Selected spectral data: $^1$H-NMR (300 MHz, CDCl$_3$) δ 6.81 (s, 1H), 6.66 (s, 1H), 3.87 (s, 3H), 3.76 (d, J=10 Hz) and 3.29 (t, J=7 Hz) (total 1H, ratio 2:1), 0.95 (t, J=7 Hz, 3H), 0.83 and 0.80 (s, total 3H). FT-IR (neat) 3411, 2923, 1504, 1446, 1267, 1202, 1118, 1024 cm$^{-1}$. Anal. Calcd for C$_{22}$H$_{32}$O$_3$, ¼ H$_2$O: C, 75.71; H, 9.39. Found: C, 75.61; H, 9.33.

EXAMPLE 18

16β-n-butyl-2-methoxyestradiol

Selected spectral data: $^1$H-NMR (300 MHz, CDCl$_3$) δ 6.81 (s, 1H), 6.66 (s, 1H), 5.43 (s, 1H), 3.88 (s, 3H), 3.76 (d, J=10 Hz) 3.29 (d, J=8 Hz) (total 1H, ratio 2.6:1), 0.83 and 0.80 (s, total 3H). FT-IR (neat) 3221, 2921, 1594, 1504, 1416, 1265, 1200, 1021 cm$^{-1}$. Anal. Calcd for C$_{23}$H$_{34}$O$_3$: C, 77.04; H, 9.56. Found: C, 77.06; H, 9.65.

EXAMPLE 19

16β-isobutyl-2-methoxyestradiol

Selected spectral data: $^1$H-NMR (300 MHz, CDCl$_3$) δ 6.81 (s, 1H), 6.66 (s, 1H), 5.43 (s, 1H), 3.88 (s, 3H), 3.77 (dd, J=9, 10 Hz) and 3.26 (t, J=7 Hz) (total 1 H, ratio 2:1), 0.84 and 0.80 (s, total 3H). IR (neat) 3525, 2913, 1506, 1258, 1202, 1026 cm$^{-1}$. Anal. Calcd for C$_{22}$H$_{30}$O$_3$: C, 76.69; H, 9.37. Found: C, 76.82; H, 9.47.

EXAMPLE 20

16β-methyl(dimethyl amine)-2-methoxyestradiol

Selected spectral data: $^1$H-NMR (300 MHz, CDCl$_3$) δ 6.81 (s, 1H), 6.65 (s, 1H), 3.88 (s) and 3.85 (obscured d) (total 4H), 2.28 (s, 6H), 0.87 (s, 3H). Anal. Calcd for C$_{22}$H$_{33}$O$_3$N, ¼ H$_2$O: C, 72.59; H, 9.28; N, 3.85. Found: C, 72.80; H, 9.17; N, 3.66.

EXAMPLE 21

16β-methanol-2-methoxyestradiol

Selected spectral data: $^1$H-NMR (300 MHz, CDCl$_3$) δ 6.78 (s, 1H), 6.61 (s, 1H), 3.92 (d, J=11 Hz, 1H), 3.84 (s, 3H), 3.80 (d, J=10 Hz, 1H), 3.63 (d, J=8, 11 Hz, 1H), 0.83 (s, 3H). FT-IR (neat) 3283, 3091, 2919, 1602, 1513, 1445, 1204, 1119, 1013 cm$^{-1}$. Anal. Calcd for C$_{20}$H$_{28}$O$_4$: C, 72.25; H, 8.49. Found: C, 72.24; H, 8.48.

EXAMPLE 22

16α-methanol-2-methoxyestradiol

Selected spectral data: $^1$H-NMR (300 MHz, CDCl$_3$) δ 6.77 (s, 1H), 6.61 (s, 1H), 3.84 (s, 3H), 3.84 (dd, J=7, 8 Hz, 1H), 3.61 (dd, J=9, 11 Hz, 1H), 3.45 (d, J=8 Hz, 1H), 0.83 (s, 3H).

EXAMPLE 23

MDA-MB-231 In Vitro Cellular Proliferation Inhibition
MDA-MB-231 Cells and Culture Conditions FIG. 1 illustrates the antiproliferative activity in cells and tumor by 2-methoxyestradiol compounds of the present invention which are modified at the 16 position.

MDA-MB-231 human breast carcinoma cells were grown in DMEM containing 10% FCS (Hyclone Laboratories, Logan Utah.) and supplemented with 2 mM L-Glutamine, 100 units/ml penicillin, 100 μg/ml streptomycin (Irvine Scientific, Santa Anna, Calif.).
Proliferation Assays MDA-MB-231 cells were plated at 5000 cells/ml in 96-well plates. After allowing the cells to attach overnight, the appropriate fresh media were applied containing differing concentrations of 2-ME2 or derivatives thereof, as described below. Drug was dissolved in DMSO (Sigma, St. Louis, Mo.) and added to the wells in a volume of 200 μl. Cells were incubated for two days at 37° C.; at 32 h BrdU was added. BrdU cell proliferation assay (a nucleotide analogue with a fluorescein tag that is incorporated into DNA) was performed as described by the manufacturer (Roche). Each condition was prepared in triplicate and the experiments were carried out a minimum of two times. Results are presented and means±SE.

EXAMPLE 24

HUVAC In Vitro Cellular Proliferation Inhibition
HUVAC Cells and Culture Conditions HUVAC cells were grown in EGM (Clonetics)
Proliferation Assays HUVEC cells were plated at 5000 cells/ml in 96-well plates. After allowing the cells to attach overnight, the cells were washed with PBS and incubated in the absence of growth factor for 24 h (EBM, 2% FCS, Clonetics). Cells were treated with increasing concentrations of drug in EBM containing 2% FCS and 10 ng.ml bFGF for 48 h at 37° C. Drug preparation, volumes added and BrdU proliferation assay were performed as indicated above.
Results The breast cancer cell line activities and the cell panels most sensitive to selected analogs are shown in Table 2.

TABLE 2

| R | α/β ratio at position 16 | HUVEC IC$_{50}$ (μM) | MDA-MB-231 IC$_{50}$ (μM) |
|---|---|---|---|
| H | N/A | 0.5 | 0.9 |
| methyl (—CH$_3$) | All alpha | <0.5 | <0.5 |
| methyl | 1:2 | 1.3 | 5 |
| ethyl (—CH$_2$CH$_3$) | 1:1 | 2 | 3 |
| n-propyl (—CH$_2$CH$_2$CH$_3$) | 7.3:1 | 6 | >50 |

TABLE 2-continued

| R | α/β ratio at position 16 | HUVEC IC$_{50}$ ($\mu$M) | MDA-MB-231 IC$_{50}$ ($\mu$M) |
|---|---|---|---|
| n-propyl | 1:2 | 9 | 36 |
| i-butyl | 1:2 | 7.5 | 40 |
| (—CH$_2$CHCH$_3$) with CH$_3$ branch | | | |
| n-butyl (—CH$_2$CH$_2$CH$_2$CH$_3$) | 2:1 | 25 | 82 |
| n-butyl | 1:2.6 | 9 | 39 |
| methanol (—CH$_2$OH) | All alpha | 15 | 22 |
| methanol | All beta | 5 | 50 |
| Methyl-dimethylamine (—CH$_2$NCH$_3$) with CH$_3$ branch | All beta | 9 | 22 |

2-Methoxyestradiol is a potent anti-angiogenic and anti-tumor agent. In order to assess the biological activity of modifications at position 16, the anti-proliferative activity of these analogs was evaluated on human umbilical vein endothelial cells (HUVEC) and breast carcinoma cell line, MDA-MB-231 as models for the anti-angiogenic and anti-tumor activity, respectively. It was found that a moderate decrease (approximately 18 fold) in anti-proliferative activity occurs as steric bulk increased (note trend from R=Et to R=Bu). The most active compound in this series is 16α-methyl, which has greater activity than 2-methoxyestradiol.

The MDA-MB-231 tumor cell line, has a much greater sensitivity to substitutions at position 16 compared to HUVEC cells. Any group at position 16 larger than ethyl has a significant decrease in antiproliferative activity (IC$_{50}$>22 $\mu$M). Of the active compounds, 16α-methyl has better activity than 2-methoxyestradiol, whereas 16β-methyl (which is a 1:2 mixture of α:β, so the presence of the α isomer may account for this activity) has about 5-fold less activity than 2-methoxyestradiol, and racemic 16-ethyl has about a 3-fold drop in activity compared to 2-methoxyestradiol.

These data suggest that it is possible to design compounds that are selective anti-angiogenic agents. For example, 16α-propyl is greater than ten-fold less active in inhibiting tumor growth while it has good activity inhibiting endothelial cell proliferation. Other examples include: 16β-propyl (4-fold difference), 16β-i-butyl (5-fold difference), 16β-n-butyl (4-fold difference) and 16β-methanol (10-fold difference). Additionally, a small alkyl group at position 16 can be added without significantly impacting the anti-proliferative activity of the molecule.

All of the publications mentioned herein are hereby incorporated by reference in their entireties. The above examples are merely demonstrative of the present invention, and are not intended to limit the scope of the appended claims.

We claim:
1. A compound of the general formula:

wherein:
a) R$_a$ is —N$_3$, —C≡C—R, —CH═CH—R, —R—CH═CH$_2$, —C≡CH, —R—R$_1$, —OC(O)CH$_3$, —C(O)H, —NH$_2$, —NMe$_2$, or —NHMe, where R is a straight or branched alkyl with up to 10 carbons or aralkyl, and R$_1$ is —OH, —NH$_2$, —Cl, —Br, —I, —F or CF$_3$;
b) R$_{h1}$ and R$_{h2}$ are independently H, or a straight or branched chain alkyl, alkenyl or alkynyl with up to 6 carbons that is unsubstituted, or substituted with one or more groups selected from a hetero functionality (O—Y, N—Y$_2$ or S—Y) where Y is independently selected from H, Me or an alkyl chain up to 6 carbons; a halo functionality (F, Cl, Br or I); an aromatic group optionally substituted with hetero, halo or alkyl; or R$_{h1}$ and R$_{h2}$ are independently an aromatic group optionally substituted with hetero, halo or alkyl, provided that both R$_{h1}$ and R$_{h2}$ are not H; and wherein all monosubstituted substituents have either an α or β configuration.

2. The compound of claim 1, wherein:
R$_{h1}$ and R$_{h2}$ are independently H and Et.

3. The compound of claim 1 wherein:
R$_{h2}$ and R$_{h2}$ are independently H and n-Pr.

4. The compound of claim 1 wherein:
R$_{h1}$ and R$_{h2}$ are independently H and i-Bu.

5. The compound of claim 1 wherein:
R$_{h1}$ and R$_{h2}$ are independently H and CH$_2$OH.

6. The compound of claim 1 wherein:
R$_{h1}$ and R$_{h2}$ are independently H and n-Bu.

7. The compound of claim 1, wherein:
R$_{h1}$ and R$_{h2}$ are independently H and Me.

8. The compound of claim 1, wherein:
R$_{h1}$ and R$_{h2}$ are independently H and (CH$_2$)$_n$(Me)$_2$, wherein
n is from 1 to 6.

* * * * *